US009211066B2

(12) United States Patent
Johnson et al.

(10) Patent No.: US 9,211,066 B2
(45) Date of Patent: Dec. 15, 2015

(54) METHOD FOR DETECTING DAMAGE TO SILICONE IMPLANTS AND COMPUTED TOMOGRAPHY DEVICE

(71) Applicants: SIEMENS AKTIENGESELLCHAFT, Munich (DE); Klinikum der Universität München, Munich (DE)

(72) Inventors: Thorsten Johnson, Munich (DE); Bernhard Krauβ, Burgthann (DE)

(73) Assignee: Siemens Aktiengesellschaft, Munich (DE)

( * ) Notice: Subject to any disclaimer, the term of this patent is extended or adjusted under 35 U.S.C. 154(b) by 150 days.

(21) Appl. No.: 13/939,308

(22) Filed: Jul. 11, 2013

(65) Prior Publication Data
US 2014/0064587 A1 Mar. 6, 2014

(30) Foreign Application Priority Data

Aug. 31, 2012 (DE) .......................... 10 2012 215 515

(51) Int. Cl.
*G06K 9/00* (2006.01)
*A61B 5/00* (2006.01)
*A61B 6/12* (2006.01)
*A61B 6/03* (2006.01)
(Continued)

(52) U.S. Cl.
CPC ............. *A61B 5/0033* (2013.01); *A61B 5/4851* (2013.01); *A61B 6/032* (2013.01); *A61B 6/12* (2013.01); *A61B 6/482* (2013.01); *A61B 6/5205* (2013.01); *G06T 7/0012* (2013.01)

(58) Field of Classification Search
None
See application file for complete search history.

(56) References Cited

U.S. PATENT DOCUMENTS 5,133,020 A * 7/1992 Giger et al. ................... 382/128
5,834,215 A * 11/1998 Garry et al. ................... 435/7.9
(Continued)

FOREIGN PATENT DOCUMENTS

CN 1551745 A 12/2004
CN 1705457 A 12/2005
(Continued)

OTHER PUBLICATIONS

Wang et al. "Material separation in x-ray CT with energy resolved photon-counting detectors," Med. Phys. 38(3), Mar. 2011, p. 1534-1546.*
(Continued)

*Primary Examiner* — Barry Drennan
*Assistant Examiner* — Samah Beg
(74) *Attorney, Agent, or Firm* — Harness, Dickey & Pierce

(57) ABSTRACT

A method is disclosed for detecting damage to silicone implants. In an embodiment, the method includes taking at least two computed tomography recordings at different X-ray spectra or different mono-energies of the X-ray radiation and reconstruction thereof. A data point is determined in a diagram for each voxel of interest, the X-ray attenuation values for different X-ray energies being plotted against one another; The data point, or another value for each voxel of interest determined from the X-ray attenuation values, is compared to known data points or values of body tissue and/or of silicone, and a note or warning is output if the data point or other value deviates from the known data points or values for body tissue by at least a first threshold value and/or in the event of simultaneous approximation to the known data point or value for silicone by less than a second threshold value.

14 Claims, 3 Drawing Sheets

(51) Int. Cl.
*A61B 6/00* (2006.01)
*G06T 7/00* (2006.01)

(56) References Cited

U.S. PATENT DOCUMENTS

| | | | |
|---|---|---|---|
| 6,370,223 B1 * | 4/2002 | Gleason et al. | 378/58 |
| 7,769,132 B1 * | 8/2010 | Hurd et al. | 378/57 |
| 2004/0101088 A1 | 5/2004 | Sabol | |
| 2004/0184574 A1 | 9/2004 | Wu et al. | |
| 2005/0020924 A1 * | 1/2005 | Mitra | 600/474 |
| 2006/0109953 A1 * | 5/2006 | Walter et al. | 378/5 |
| 2007/0183568 A1 * | 8/2007 | Kang et al. | 378/57 |
| 2007/0217570 A1 | 9/2007 | Grasruck et al. | |
| 2007/0249933 A1 * | 10/2007 | Krauss | 600/425 |
| 2008/0013672 A1 * | 1/2008 | Krauss et al. | 378/4 |
| 2008/0037699 A1 * | 2/2008 | Krauss | 378/4 |
| 2008/0253508 A1 * | 10/2008 | Krauss | 378/19 |
| 2009/0296884 A1 * | 12/2009 | Honda et al. | 378/62 |
| 2010/0166273 A1 * | 7/2010 | Wismuller | 382/131 |
| 2010/0195885 A1 * | 8/2010 | Ma | 382/131 |
| 2011/0158491 A1 * | 6/2011 | Markova et al. | 382/128 |
| 2012/0302874 A1 * | 11/2012 | Hollstien | 600/424 |
| 2013/0129180 A1 * | 5/2013 | Kang et al. | 382/132 |
| 2014/0056503 A1 * | 2/2014 | Shechter | 382/131 |

FOREIGN PATENT DOCUMENTS

| | | |
|---|---|---|
| CN | 101028199 A | 9/2007 |
| CN | 101044986 A | 10/2007 |
| DE | 102006009222 A1 | 9/2007 |
| DE | 102006015452 A1 | 10/2007 |

OTHER PUBLICATIONS

Chinese Office Action for CN Patent Application No. 2013103831337 dated Apr. 3, 2015 and English translation.

* cited by examiner

METHOD FOR DETECTING DAMAGE TO SILICONE IMPLANTS AND COMPUTED TOMOGRAPHY DEVICE

PRIORITY STATEMENT

The present application hereby claims priority under 35 U.S.C. §119 to German patent application number DE 102012215515.5 filed Aug. 31, 2012, the entire contents of which are hereby incorporated herein by reference.

FIELD

At least one embodiment of the invention generally relates to a method for detecting damage to silicone implants in a human body by way of a computed tomography device.

BACKGROUND

The detection of damage to silicone implants permanently introduced into the human body is of current interest. If such a silicone implant is damaged, silicone can escape and penetrate into the surrounding tissue of the body. To prevent possible impairments to health by the silicone, leaking implants must be removed as quickly as possible. One problem that exists here is that this type of damage to a silicone implant first has to be discovered.

Certain possibilities are known for detecting damage to silicone implants, e.g. magnetic resonance tomography, ultrasound or computed tomography. In this case magnetic resonance tomography is a well suited method of detection, but it cannot be used for every patient and is moreover very expensive. In addition the positioning of the patient compared to a subsequent surgical intervention must be changed here, which makes it more difficult to plan any operation. Ultrasound measurement generally does not permit a 3D representation of the object region, so that the rear of the implant is not visible.

Taking an individual computed tomography recording frequently produces uncertain results. Because silicone implants have a physical density which is close to soft tissue (since after all the implants are not supposed to be perceived as foreign bodies), the CT value of the silicone used is close to that of soft tissue and relatively unspecific. Major damage to the implant shell whereby silicone material is obviously escaping is generally visible, but minor damage and tears whereby small quantities of silicone escape from the implant cannot be detected unequivocally.

SUMMARY

At least one embodiment of the present invention is directed to a method which permits the detection of silicone in the human body even in small quantities. At least one embodiment is further directed to an X-ray device suitable for the performance of the method.

A method is disclosed for detecting damage to silicone implants in a human body by way of a computed tomography device. Advantageous embodiments of the invention are the subject matter of each of the associated subclaims.

A method of at least one embodiment for detecting damage to silicone implants in an object region of a human body by way of a computed tomography device comprises:
a) Taking at least two computed tomography recordings of the object region at different X-ray spectra or different mono-energies of the X-ray radiation,
b) Reconstruction of the at least two computed tomography recordings to form 3D data sets which contain X-ray attenuation values or equivalent material densities in terms of a basic material decomposition of voxels of the object region,
c) Determination of a data point in a diagram for each voxel of interest, the X-ray attenuation values for different X-ray energies being plotted against one another,
d) Comparison of the data point or of another value determined from the X-ray attenuation values for each voxel of interest with known data points or values of body tissue and/or of silicone, and
e) Output of a note or warning if the data point or the other value deviates from the known data points or values for body tissue by at least a predefined first threshold value and/or in the event of simultaneous approximation to the known data point or value for silicone by less than a second threshold value.

BRIEF DESCRIPTION OF THE DRAWINGS

The invention and other advantageous embodiments according to features of the subclaims are explained in greater detail below in the drawing on the basis of schematically illustrated example embodiments, without thereby limiting the invention to these example embodiments. In the drawings:

DETAILED DESCRIPTION OF THE EXAMPLE EMBODIMENTS

Figure 1:
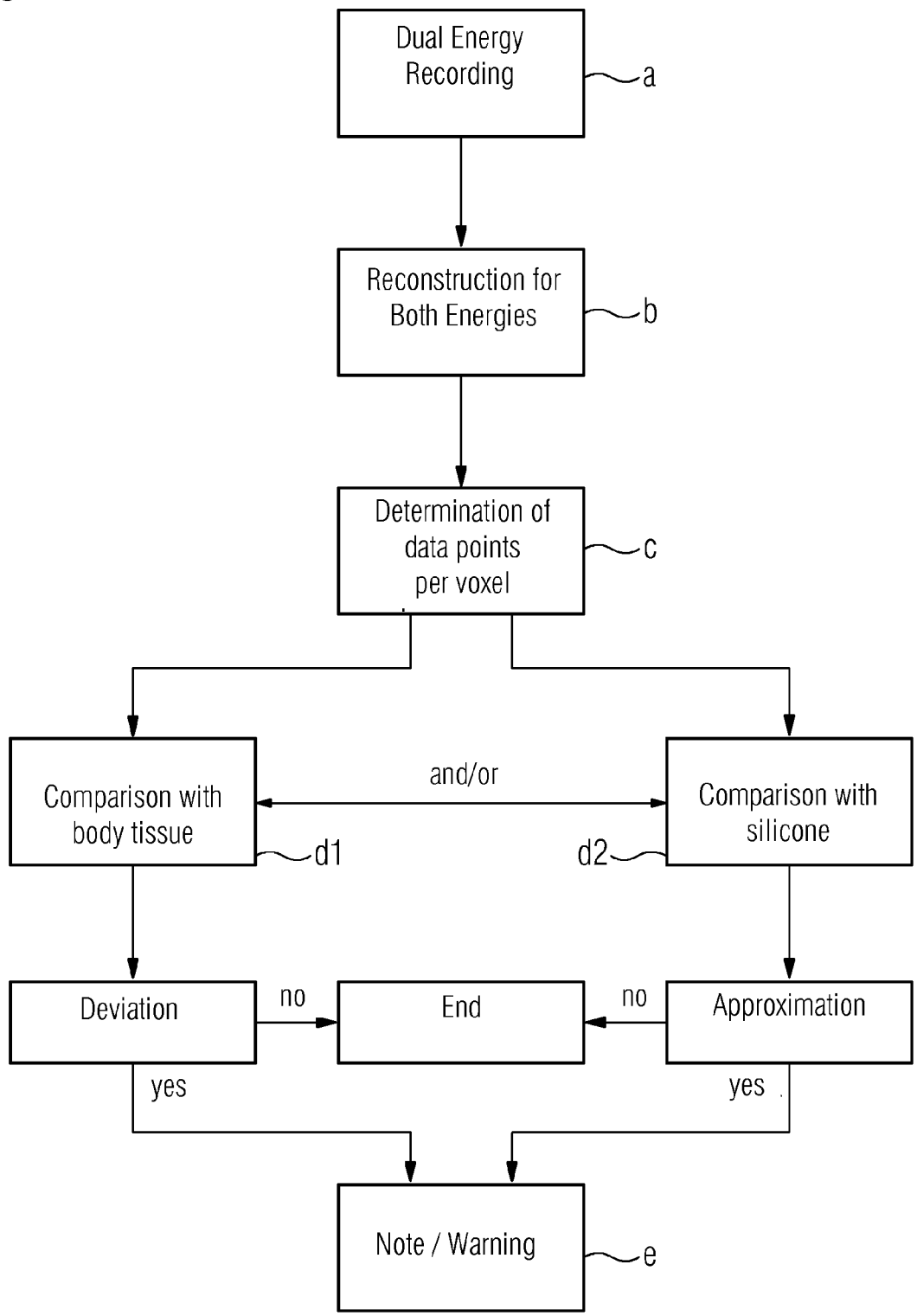
FIG. 1 shows a sequence of an embodiment of the inventive method.

The present invention will be further described in detail in conjunction with the accompanying drawings and embodiments. It should be understood that the particular embodiments described herein are only used to illustrate the present invention but not to limit the present invention.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

A method is disclosed for detecting damage to silicone implants in a human body by way of a computed tomography device. Advantageous embodiments of the invention are the subject matter of each of the associated subclaims.

A method of at least one embodiment for detecting damage to silicone implants in an object region of a human body by way of a computed tomography device comprises:

f) Taking at least two computed tomography recordings of the object region at different X-ray spectra or different mono-energies of the X-ray radiation, g) Reconstruction of the at least two computed tomography recordings to form 3D data sets which contain X-ray attenuation values or equivalent material densities in terms of a basic material decomposition of voxels of the object region, h) Determination of a data point in a diagram for each voxel of interest, the X-ray attenuation values for different X-ray energies being plotted against one another, i) Comparison of the data point or of another value determined from the X-ray attenuation values for each voxel of interest with known data points or values of body tissue and/or of silicone, and j) Output of a note or warning if the data point or the other value deviates from the known data points or values for body tissue by at least a predefined first threshold value and/or in the event of simultaneous approximation to the known data point or value for silicone by less than a second threshold value.

Thanks to the inventive method of at least one embodiment, an escape of silicone from a silicone implant into the surrounding body tissue can be easily, automatically and unequivocally detected for every object region of interest even in very small quantities and thus also any minor damage to the implant. At least one embodiment of the invention is based on the knowledge that the X-ray attenuation values of silicone from an individual computed tomography recording are very close to those of soft tissue, but that when computed tomography recordings at different radiation spectra are compared a significant difference can be identified. By automatically comparing the values of the object region of interest with known values for body tissue and for silicone, any damage to the implant can thus be detected with a high probability. The threshold values can in this case be selected accordingly. Thanks to the method it is also easier to plan operations for a subsequent surgical intervention to remove the implant or the silicone that has escaped.

The note or warning may for example be an optical, e.g. colored, marking of the affected regions on a display of CT images, possibly after three-dimensional reformatting of the images. A complex display of the affected data points in the diagram or of a 3D volume display of the object region or a text display may also be provided, for example.

If necessary noise reduction and/or artifact correction can be carried out at any time in order to purge the data points in the diagram of measurement errors. According to one embodiment of the invention, the attenuation coefficients $\mu$ or the CT values for each voxel of interest are plotted as X-ray attenuation values in a diagram or a table and the data points are compared with known values. The linear attenuation coefficient or absorption coefficient $\mu$ generally describes the attenuation of the intensity of electromagnetic radiation when passing through a material. The CT value, which is measured in Hounsfield units (HU), is derived by definition from the attenuation coefficient of the current material and that of water:

$$[CT-\text{Value}] := \frac{\mu - \mu_{Water}}{\mu_{Water}} \cdot 1000\ HU$$

In order to reduce deviations of the measured CT value caused by so-called beam hardening, a known correction method (raw-data-based dual energy CT method, especially for calculating mono-energy images; iterative method with forward projection of segmented image regions) can be used here.

According to another embodiment of the invention, at least one effective atomic number or an equivalent material density in terms of a basic material decomposition is determined from the X-ray attenuation values and for each voxel of interest is compared with the known effective atomic numbers or equivalent material densities of body tissue and silicone. Using the at least two computed tomography recordings, an effective atomic number and equivalent material density can be unequivocally calculated. In particular, in these values no similarity can any longer be identified between body tissue and silicone, so that silicone can be detected even more effectively.

In addition, using raw-data-based methods it is also possible to undertake a basic material decomposition, without attenuation values being calculated beforehand. In this case these material densities are entered into the diagram. Building on this, all other values mentioned can be determined from the equivalent material densities of the two basic materials.

According to another configuration of the invention, any combination of soft tissue and fat is used as a comparison value for the body tissue. Both these types of tissue generally describe very well the properties of body tissue, in particular in the region of the breast, which represents the main area of use of silicone implants. As an advantageous example embodiment for the situation in which the body tissue is regarded as any combination of soft tissue and fat, a perpendicular distance of the data point from a connecting straight line between the known values of soft tissue and fat is determined and compared with the first threshold value. If the first threshold value is exceeded and simultaneously the known data point for silicone is approximated by less than a second threshold value, the note or warning is output.

According to another embodiment of the invention, three or more computed tomography recordings of the object region are taken at different radiation spectra or different mono-energies of the X-ray radiation. A more complex determination of X-ray attenuation values or data points and corresponding comparisons can then be carried out here and even more unequivocal detection of silicone can be achieved.

Regardless of which of the variables mentioned is used to detect the silicone, the data point can also be mapped to a measured value by means of a predefined table. The table contains the measured values for a fixed number of attenuation values at low and high tube voltage. The measured value is then obtained by suitable interpolation of the adjacent table values.

To perform the method use can be made of a computed tomography device which has a dual-energy recording unit for taking at least two computed tomography recordings of the object region at different radiation spectra or different mono-energies of the X-ray radiation as well as a system controller with a computing unit for reconstruction of the computed tomography recordings and for carrying out steps c and d as well as an output unit for carrying out step e of the method.

FIG. 1 shows an example of a sequence of an embodiment of an inventive method.

Initially in a first step a) at least two computed tomography recordings of the object region are taken at a different spectral distribution of the X-ray radiation. To take the computed tomography recordings use is made of a multi-energy computed tomography device, e.g. a so-called dual-energy computed tomography device, with which it is possible to record at least two computed tomography recordings with a different spectral distribution of the X-ray radiation or different X-ray energy simultaneously or virtually simultaneously. Different spectral distributions or different X-ray energies can for example be obtained using different tube voltages of the X-ray tube used.

In a second step b) (at least) two 3D data sets which contain X-ray attenuation values of voxels of the object region at the respective spectral distribution of the X-ray radiation are reconstructed from the raw data of the two computed tomography recordings. X-ray attenuation values can here refer both to the linear attenuation coefficients $\mu$ and also, for example, the CT value derived therefrom or equivalent material densities in terms of a basic material decomposition. In addition, smoothing filters or correction algorithms can be used before or after the reconstruction in order to compensate for noise, measurement errors or blurring.

In a third step c) for each voxel of interest of the object region a data point is determined in a diagram or a table in which the X-ray attenuation values for different spectral distributions or X-ray energies are plotted against one another. For example, for a voxel the CT value at a high X-ray energy on one axis of the diagram is plotted against the CT value at a low X-ray energy on the second axis of the diagram. The corresponding data points are used as a basis for the following evaluation; they can for example also be displayed on a display unit.

Figure 4:
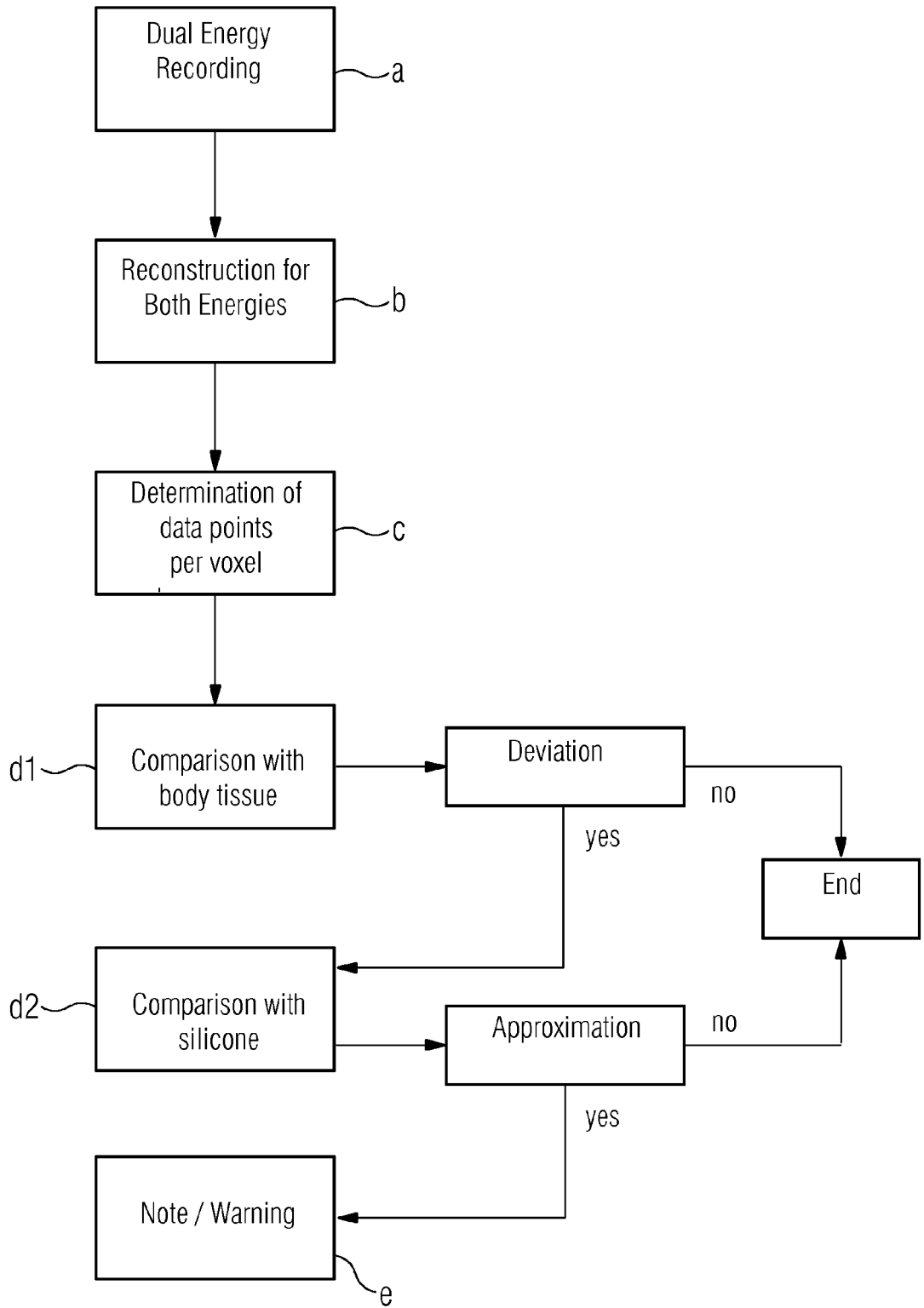

In a fourth step d), for each voxel of interest the data point or another value determined from the X-ray attenuation values is compared with known data points or values of body tissue and/or of silicone. The fourth step d) can in this case be split into two sub-steps. The first sub-step d1) comprises the comparison with known values of body tissue and the second sub-step d2) the comparison with known values of silicone, not necessarily in this order. In each case only one of the sub-steps can be performed, as shown in FIG. 1, or alternatively both sub-steps can be performed, as shown in FIG. 4.

For the first sub-step d1) the data point of the CT values for the voxels of interest plotted against one another is thus for example compared to a known data point for soft tissue or fat or a mixture of the two. For the comparison, the distance between the data point of the voxel of interest and the known value is in particular determined and compared to a first, e.g. previously fixed, threshold value.

If for example a mixture of soft tissue and fat is to be expected in an unknown composition, then advantageously a perpendicular distance of the data point of the voxel of interest from a connecting straight line which connects the known data points for fat and for soft tissue can be calculated. A data point of body tissue which consists of any mixture of soft tissue and fat (as well as water) definitely lies on such a connecting straight line between the pure substances of soft tissue and fat. In contrast, if the data point is at a distance from the connecting straight line, then in all probability there is another material in the body tissue. Such a method for 3-material decomposition is known for example from DE 10 2006 009 222 A1, the entire contents of which are incorporated herein by reference.

Figure 3:
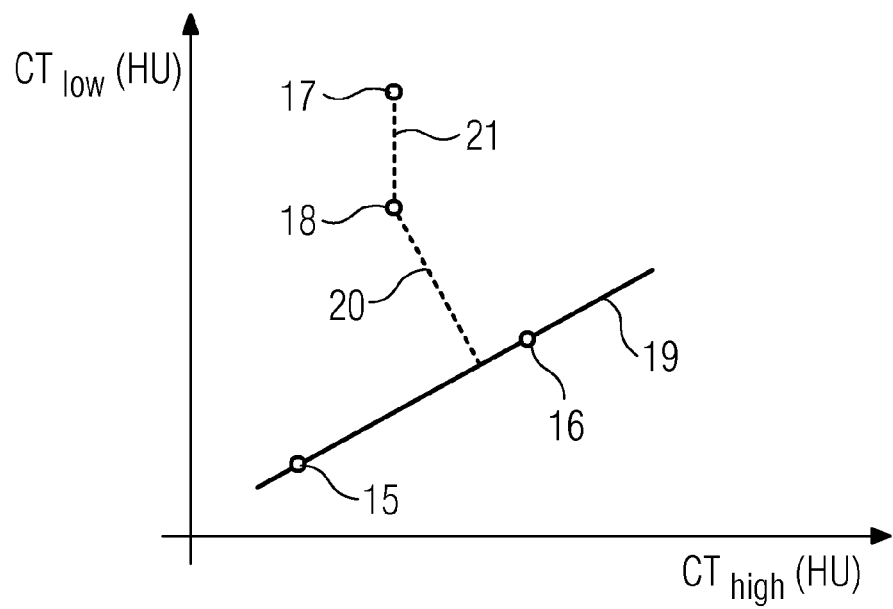
FIG. 3 shows a diagram with specimen values plotted against one another to clarify an embodiment of the inventive method and FIG. 4 shows a sequence of an embodiment of an alternative inventive method.

FIG. 3 shows an example of the data point for fat 15 and the data point for soft tissue 16, with CT values of high X-ray energy CThigh plotted against CT values of low X-ray energy CTlow, the connecting straight line 19 likewise being illustrated. The data point of the voxel 18 of interest has a perpendicular distance 20, as indicated by a dashed line, from the connecting straight line 19.

Alternatively another value such as for example the effective atomic number or the material density can also be determined from the X-ray attenuation values for each voxel of interest and can be compared to the known effective atomic numbers or material densities of body tissue (here once again e.g. fat, soft tissue or a mixture of both). The comparison includes in particular a determination of the distance of the values from one another and the comparison with the first threshold value previously fixed in this connection.

For the second sub-step d2) the data point of the CT values for the voxels of interest plotted against one another is for example compared to a known data point for silicone, the distance between the data point of the voxel of interest and the known value in particular being determined and compared to a second threshold value fixed beforehand, for example. This is likewise shown in FIG. 3, the data point of the voxel 18 of interest having a distance 21 from a known data point for silicone 17. The plotting can alternatively also show other X-ray attenuation values such as the linear attenuation coefficient m. The effective atomic number or the equivalent material densities can also be compared to the values for silicone. The data point for the corresponding silicone being searched for (fluctuations can also occur here, e.g. depending on the manufacturer) can also be measured beforehand.

FIG. 4 shows that both sub-steps are performed, the first sub-step d1 first and then the second sub-step d2. Alternatively this can also be performed the other way round.

In a fifth step e) a note or a warning is output or displayed, if the distance of the data point of the voxel of interest or another value deviates from body tissue (e.g. fat, soft tissue, mixture of fat and soft tissue in the form of the connecting straight line) by at least a first threshold value or deviates from silicone by less than a second threshold value or alternatively if both conditions are met. The note or warning can take many forms. For example, text or a graph containing the corresponding markings can be output on a display unit (e.g. a monitor). A 3D display of the object region can also be shown in which the critical voxels are overlaid in a signal color or are flashing. Color coding (e.g. red/yellow/green) is possible here in conjunction with multiple threshold levels for the first threshold value and the second threshold value. In particular, the 3D displays can be used for planning operations if the damaged implant is to be removed after the examination. For this, it is also possible and relevant to display contaminated tissue and lymph nodes.

When using three or more computed tomography recordings at different spectral distributions or X-ray energies (multi-energy CT) the data point can be plotted in the multi-dimensional point. Here too a comparison with threshold values can correspondingly be performed. The silicone here lies in an unequivocal region of the three- or multi-dimensional space, so that it is unequivocally possible to detect silicone in the body tissue.

Figure 2:
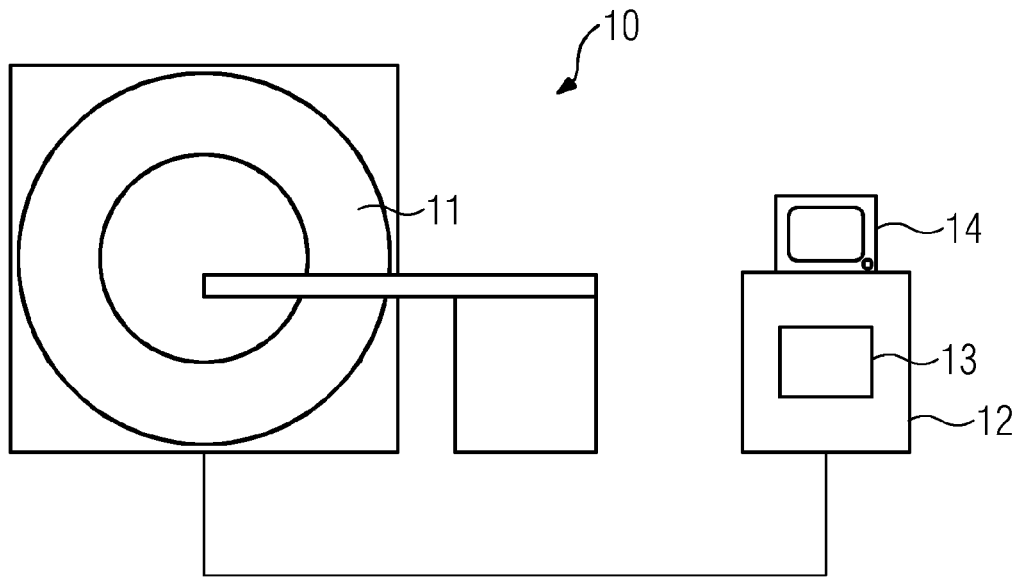
FIG. 2 shows a view of an apparatus for carrying out an embodiment of the method.

FIG. 2 shows a computed tomography device 10 which is configured to execute the inventive method. It may be formed by a dual-energy computed tomography device or a multi-energy computed tomography device. The computed tomography device 10 has a rotating gantry 11, which has a recording system containing at least one line detector and at least one X-ray source. The recording system is here configured to record at least two computed tomography recordings of an object region at different radiation spectra or different mono-energies of the X-ray radiation. The configuration of such a recording system is in principle known to the person skilled in the art. For example, multiple X-ray sources at different X-ray voltage (typical values e.g. 80 kV and 140 kV), different detectors with different spectral sensitivity, different filters upstream of the X-ray sources and/or X-ray detectors or else a combination of the cited technologies may be provided.

The computed tomography device additionally has a system controller 12 which is configured to control the inventive method, and a computing unit 13 which e.g. performs the reconstruction, the determination of data points, the determination of values and the comparison with predefined threshold values. The computing unit 13 can be formed, for example, by a PC. Additionally the computed tomography device has an output unit, e.g. a monitor 14, on which a note or warning is output. Alternatively loudspeakers or other displays may also be provided.

At least one embodiment of the invention can be briefly summarized as follows: to detect even tiny damage to silicone implants a method is provided for detecting damage to silicone implants in an object region of a human body by way of a computed tomography device with the following steps: taking at least two computed tomography recordings of the object region at different X-ray spectra or different mono-energies of the X-ray radiation, reconstruction of the at least two computed tomography recordings to form 3D data sets which contain X-ray attenuation values or equivalent material densities in terms of a basic material decomposition of voxels of the object region, determination of a data point in a diagram or a table for each voxel of interest, the X-ray attenuation values for different X-ray energies being plotted against one another, comparison of the data point or of another value determined from the X-ray attenuation values for each voxel of interest with known data points or values of body tissue and/or of silicone, and output of a note or warning if the data point or other value deviates from the known data points or values for body tissue by at least a predefined first threshold value and/or in the event of simultaneous approximation to the known data point or value for silicone by less than a second threshold value.

The foregoing explanation of the embodiments describes the present invention merely by way of examples. Self-evidently, individual features of the embodiments may be freely combined with one another, where technically feasible, without departing from the scope of the present invention.

What is claimed is:

1. A method for detecting damage to silicone implants in an object region of a human body using a computed tomography device, the method comprising:
    taking at least two computed tomography recordings of the object region, each at different X-ray spectra or different mono-energies of the X-ray radiation;
    reconstructing the at least two computed tomography recordings to form 3D data sets which contain X-ray attenuation values or equivalent material densities in terms of a basic material decomposition of voxels of the object region;
    determining a data point in a diagram for each voxel of interest, the X-ray attenuation values for different X-ray energies being plotted against one another;
    comparing the data point, or another value for each voxel of interest determined from the X-ray attenuation values, with known data points or values of body tissue and known data points or values of silicone;

determining if the data point or other value for each voxel of interest deviates from the known data points or values for body tissue by at least a first threshold value;

determining if the data point or other value for each voxel of interest deviates from the known data point or value for silicone by less than a second threshold value; and outputting a warning if the data point or other value for each voxel of interest deviates from the known data points or values for body tissue by the first threshold value while the data point or other value for each voxel of interest simultaneously deviates from the known data points or values for silicone by less than the second threshold value.

2. The method of claim 1, wherein the comparing plots X-ray attenuation coefficients or CT values for each voxel of interest in a diagram and compares the data points with known values.

3. The method of claim 2, wherein the CT values of the different X-ray energies are mapped to a measured variable by interpolation of precalculated table values.

4. The method of claim 1, wherein the comparing includes,
determining at least one effective atomic number or an equivalent material density from the X-ray attenuation values, and
comparing each voxel of interest to known effective atomic numbers or equivalent material densities of body tissue and silicone.

5. The method of claim 1, wherein any combination of soft tissue and fat are used as comparison values for the body tissue.

6. The method of claim 5, wherein a note or warning is output if at least one of
a perpendicular distance of the data point from a connecting straight line between the known data points of soft tissue and fat exceeds the first threshold value, and
a second threshold value for the known data point for silicone is simultaneously exceeded.

7. The method of claim 1, wherein three or more computed tomography recordings of the object region are taken at different radiation spectra or different mono-energies of the X-ray radiation.

8. A computed tomography device, comprising:
a dual-energy recording unit configured to record at least two computed tomography recordings of the object region at different radiation spectra or different mono-energies of the X-ray radiation; and
a system controller including a computing unit, configured to reconstruct the computed tomography recordings to form 3D data sets which contain X-ray attenuation values or equivalent material densities in terms of a basic material decomposition of voxels of the object region and configured to:

determine a data point in a diagram for each voxel of interest, the X-ray attenuation values for different X-ray energies being plotted against one another, compare the data point, or another value for each voxel of interest determined from the X-ray attenuation values, with known data points or values of body tissue and known data points or values of silicone, determine if the data point or other value for each voxel of interest deviates from the known data points or values for body tissue by at least a first threshold value, determine if the data point or other value for each voxel of interest deviates from the known data point or value for silicone by less than a second threshold value, and output a warning if the data point or other value for each voxel of interest deviates from the known data points or values for body tissue by the first threshold value while the data point or other value for each voxel of interest simultaneously deviates from the known data points or values for silicone by less than the second threshold value.

9. The computed tomography device of claim 8, wherein the system controller is configured to,
plot X-ray attenuation coefficients or CT values for each voxel of interest in a diagram, and
the data points are compared with known values.

10. The computed tomography device of claim 9, wherein the CT values of the different X-ray energies are mapped to a measured variable by interpolation of precalculated table values.

11. The computed tomography device of claim 8, wherein, the system controller is configured to,
determine at least one effective atomic number or an equivalent material density from the X-ray attenuation values, and
compare each voxel of interest to known effective atomic numbers or equivalent material densities of body tissue and silicone.

12. The computed tomography device of claim 8, wherein any combination of soft tissue and fat are used as comparison values for the body tissue.

13. The computed tomography device of claim 12, wherein a note or warning is output if at least one of
a perpendicular distance of the data point from a connecting straight line between the known data points of soft tissue and fat exceeds the first threshold value, and
a second threshold value for the known data point for silicone is simultaneously exceeded.

14. The computed tomography device of claim 8, wherein three or more computed tomography recordings of the object region are taken at different radiation spectra or different mono-energies of the X-ray radiation.

* * * * *